United States Patent
Paulus

(10) Patent No.: US 8,617,382 B2
(45) Date of Patent: Dec. 31, 2013

(54) PROCESS AND DEVICE FOR EMULATING A COUNTER-ELECTRODE IN A MONOLITHICALLY INTEGRATED ELECTROCHEMICAL ANALYSIS SYSTEM

(75) Inventor: Christian Paulus, Weilheim (DE)

(73) Assignee: Siemens Aktiengesellschaft, Munich (DE)

( * ) Notice: Subject to any disclaimer, the term of this patent is extended or adjusted under 35 U.S.C. 154(b) by 1139 days.

(21) Appl. No.: 11/630,975

(22) PCT Filed: Jun. 29, 2005

(86) PCT No.: PCT/DE2005/001146
§ 371 (c)(1),
(2), (4) Date: Dec. 28, 2006

(87) PCT Pub. No.: WO2006/000207
PCT Pub. Date: Jan. 5, 2006

(65) Prior Publication Data
US 2008/0073225 A1    Mar. 27, 2008

(30) Foreign Application Priority Data
Jun. 29, 2004   (DE) .......................... 10 2004 031 370

(51) Int. Cl.
*C12Q 1/00* (2006.01)
(52) U.S. Cl.
USPC .............. 205/777.5; 204/403.01; 204/403.02; 205/778; 205/792
(58) Field of Classification Search
USPC ............. 204/403.01–403.15; 205/777.5–778, 205/779
See application file for complete search history.

(56) References Cited

U.S. PATENT DOCUMENTS

| 5,443,701 | A | * | 8/1995 | Willner et al. ............. 205/777.5 |
| 5,985,129 | A | * | 11/1999 | Gough et al. ................ 205/724 |
| 6,143,164 | A | * | 11/2000 | Heller et al. .................. 600/583 |
| 2002/0029964 | A1 | * | 3/2002 | Matsumoto .................... 204/403 |
| 2002/0039743 | A1 | | 4/2002 | Hashimoto et al. | |

(Continued)

FOREIGN PATENT DOCUMENTS

EP    0567725 A1 *   3/1993
EP    0 567 725 A   11/1993

OTHER PUBLICATIONS

C.Paulus et al.: "A fully integrated CMOS sensor system for chronocoulometry", Proceedings of IEEE Sensors 2003, $2^{nd}$. IEEE International Conference on Sensors, Toronto, Canada, Oct. 22-24, 2003, vol. 2, pp. 1329-1332, XP010690994, ISBN: 0780381335.

*Primary Examiner* — Bach Dinh
(74) *Attorney, Agent, or Firm* — Harness, Dickey & Pierce, P.L.C.

(57) ABSTRACT

A sensor array with at least three electrodes and a switching unit is disclosed, as well as a process for operating such a sensor array for implementing an electrochemical analysis process. The at least three electrodes can be selectively switched as counter-electrodes or as a working electrode which can be electrically coupled to an electrolytic analyte. The at least three electrodes are set up in such a way that sensor events occur at an electrode switched as working electrode in the electrolyte solution, in the presence of the electrolytic analyte. The electrodes which are not required as working electrodes at a particular point in time for detecting the electrolytic analyte can thus be switched together to form the counter-electrode of the sensor array, thus dispensing with the need for a separate counter-electrode.

20 Claims, 11 Drawing Sheets

(56) References Cited

U.S. PATENT DOCUMENTS

| | | | |
|---|---|---|---|
| 2003/0022150 A1* | 1/2003 | Sampson et al. | 435/4 |
| 2003/0159944 A1* | 8/2003 | Pottgen et al. | 205/777.5 |
| 2003/0186263 A1* | 10/2003 | Frey et al. | 435/6 |
| 2004/0090168 A1* | 5/2004 | Kumar et al. | 313/483 |
| 2004/0140209 A1* | 7/2004 | Choi et al. | 204/403.01 |

* cited by examiner

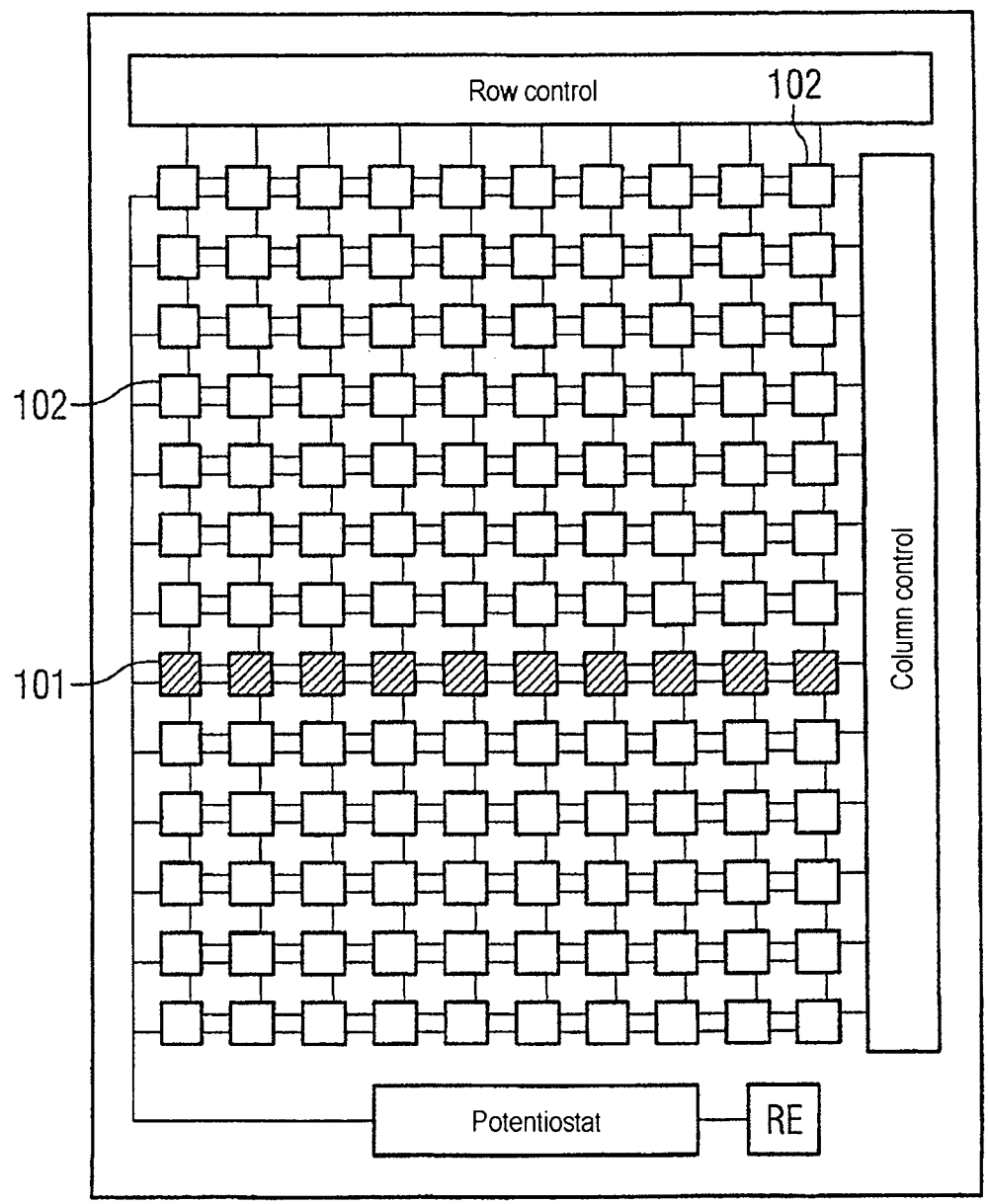

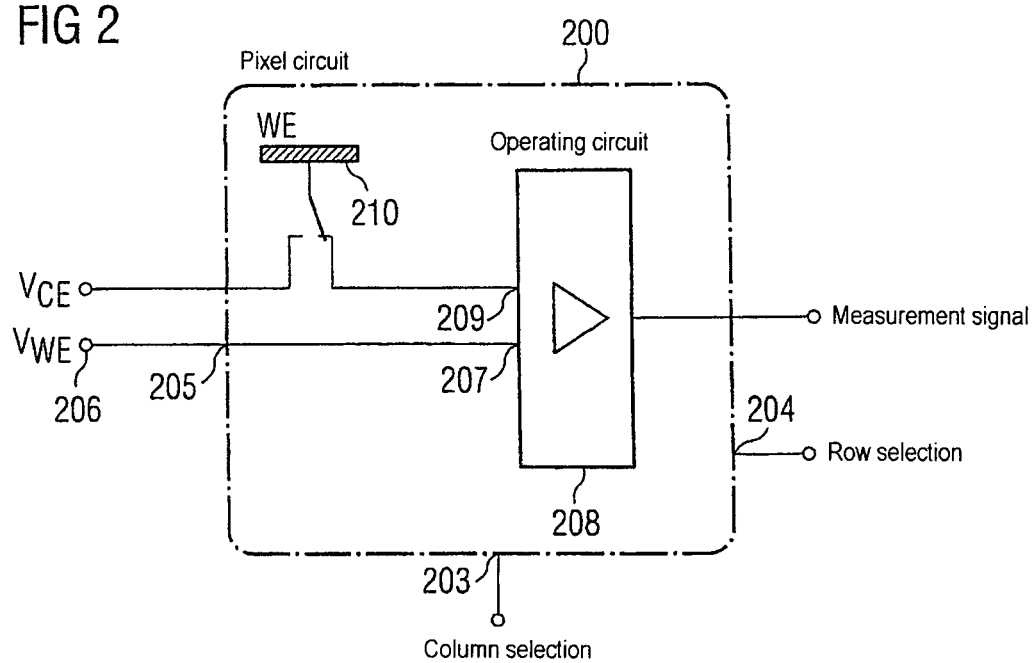
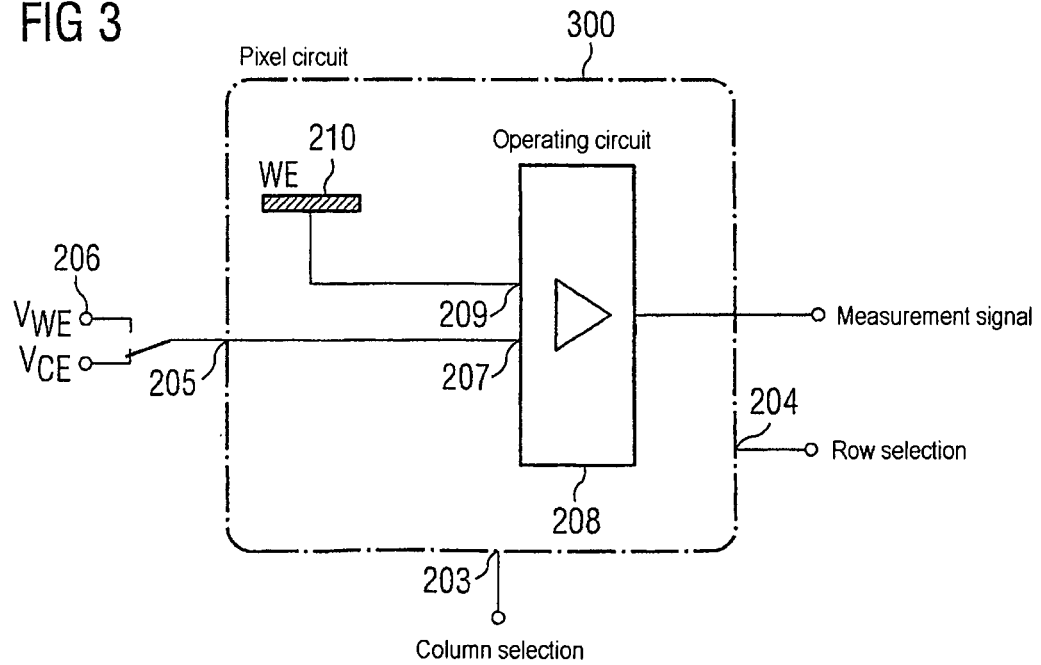

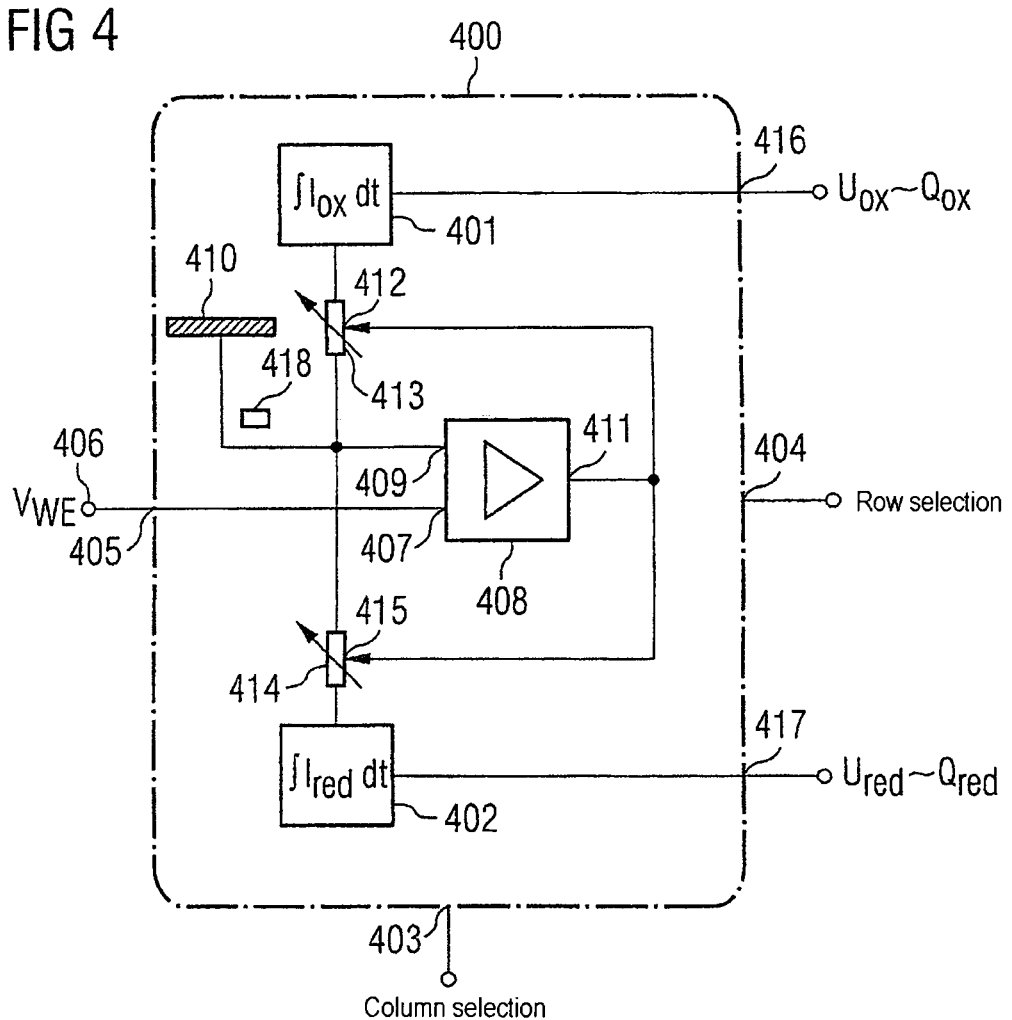

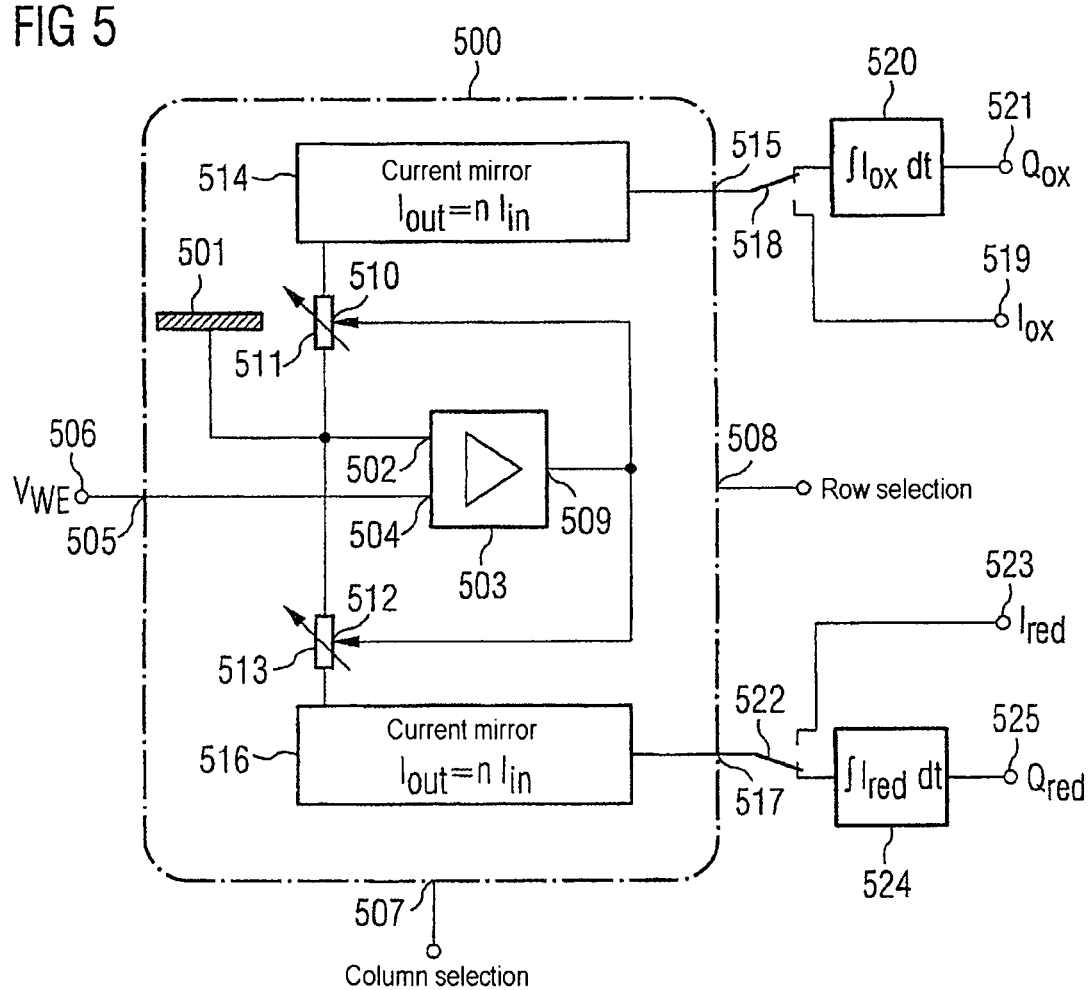

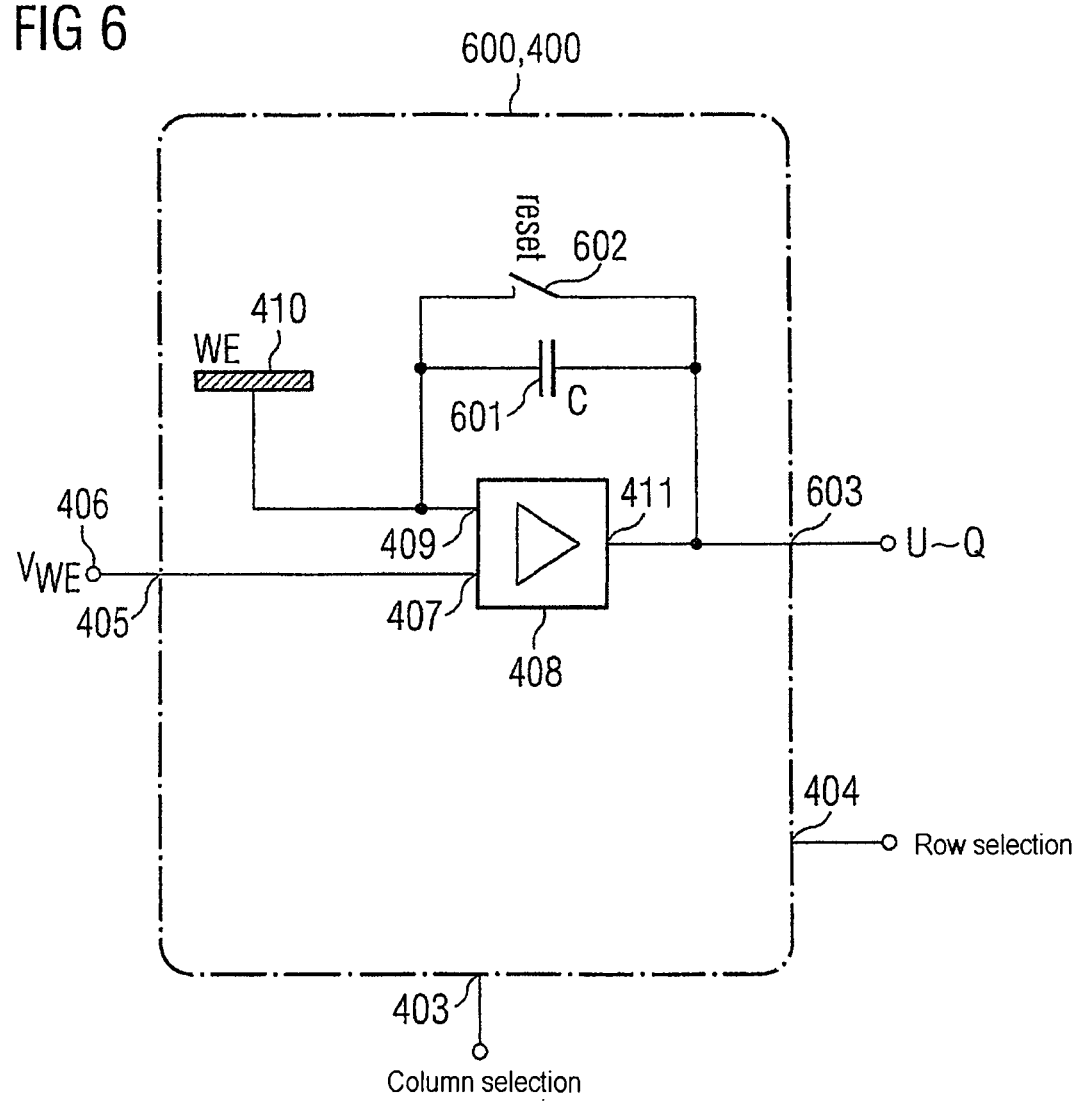

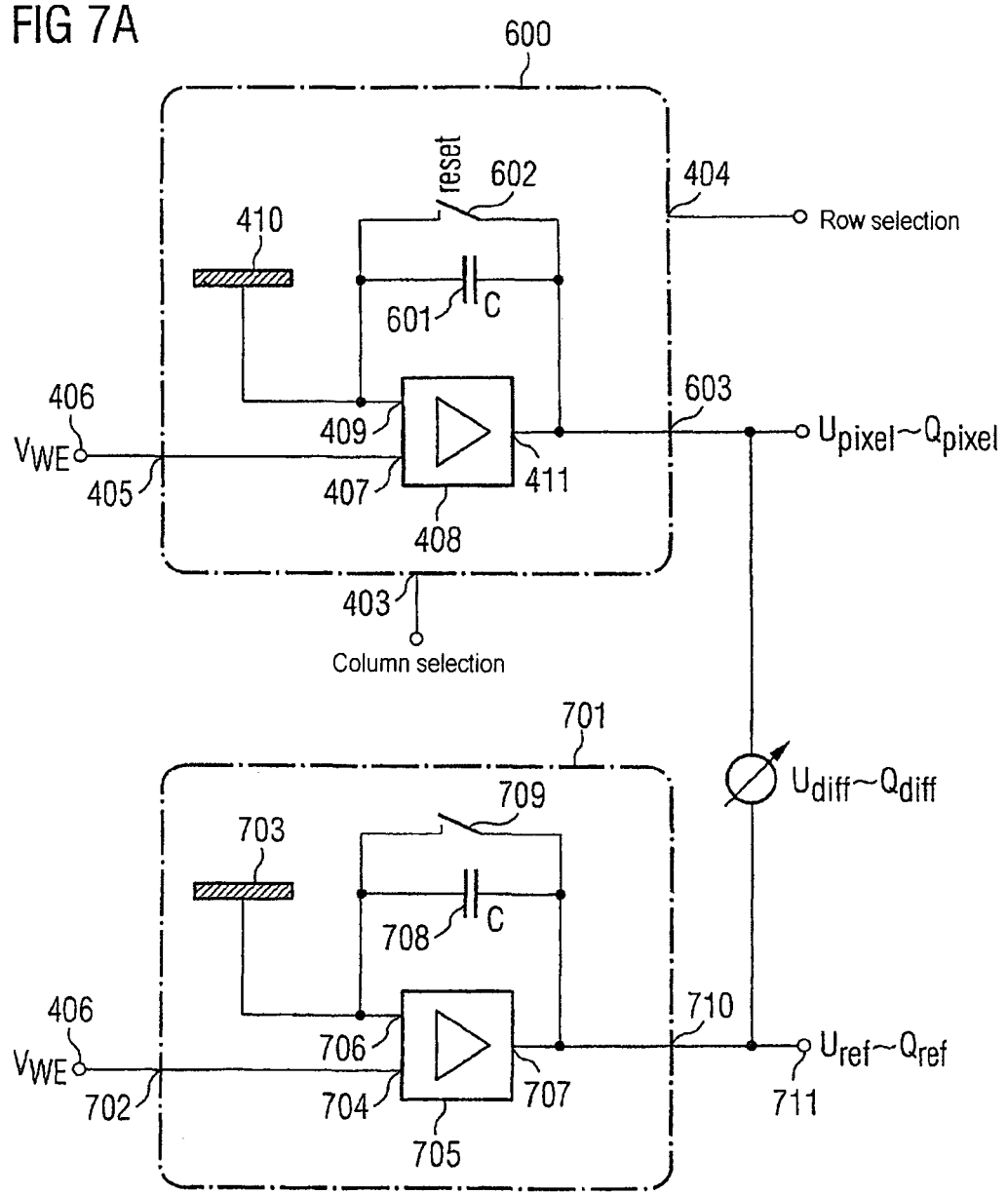

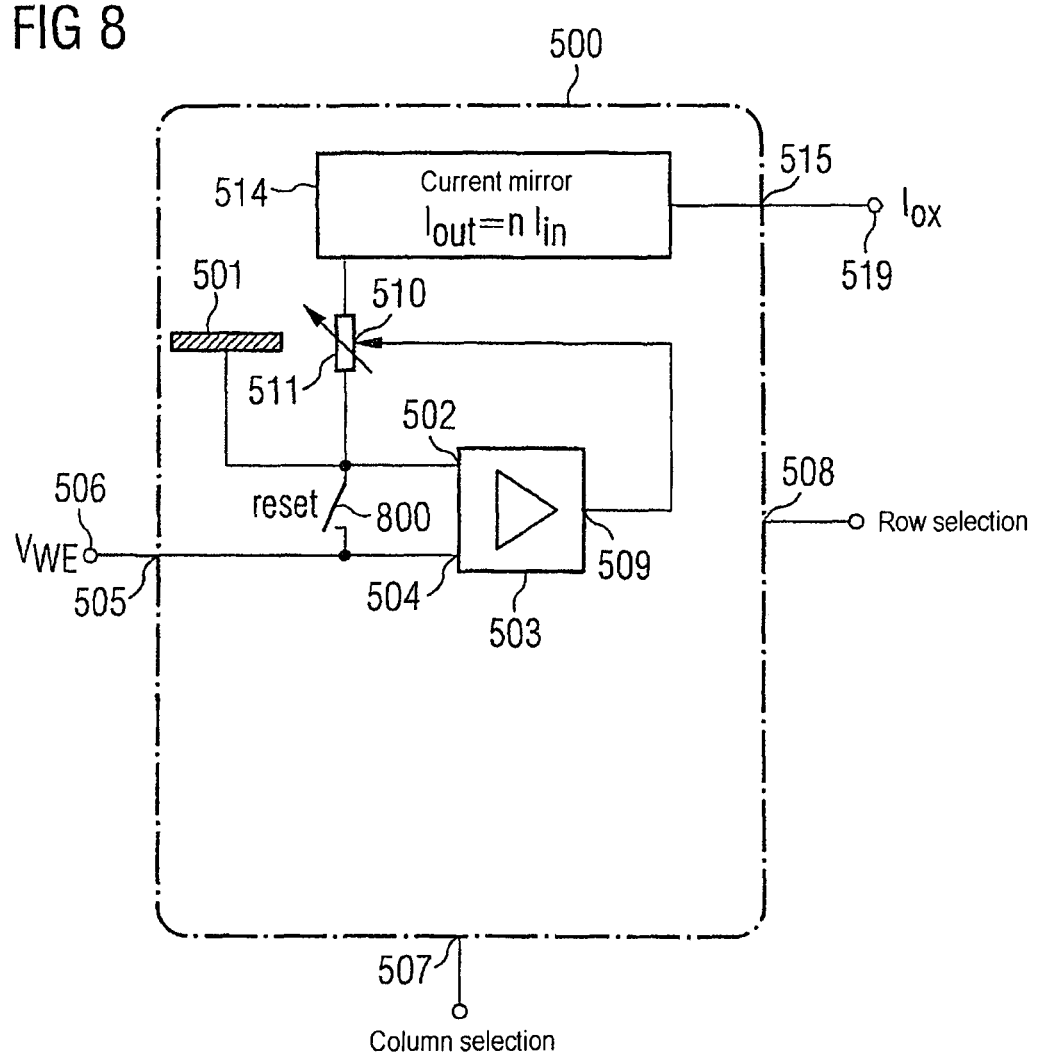

PROCESS AND DEVICE FOR EMULATING A COUNTER-ELECTRODE IN A MONOLITHICALLY INTEGRATED ELECTROCHEMICAL ANALYSIS SYSTEM

PRIORITY STATEMENT

This application is the national phase under 35 U.S.C. §371 of PCT International Application No. PCT/DE2005/001146 which has an International filing date of Jun. 29, 2005, which designated the United States of America and which claims priority on German Patent Application number 10 2004 031 370.9 filed Jun. 29, 2004, the entire contents of which are hereby incorporated herein by reference.

FIELD

Embodiments of the invention generally relate to an apparatus and/or a method for emulation of an opposing electrode in a monolithically integrated electrochemical analysis system.

BACKGROUND

An electrochemical analysis method can be used to both qualitatively and quantitatively define substances on the basis of specific physical characteristics, using electric current. Electrochemical analysis methods in which electrode reactions play a role are of particular importance. Depending on whether the excitation signal (current, voltage or potential) is kept constant, these methods are subdivided into two groups. For example, potentiometry, chronopotentiometry, coulometry, amperometry, chronoamperometry and chronocoulometry are techniques in which the excitation signal is kept constant. In voltammetric and polarographic methods, the excitation signal is varied.

Together with optical methods, electrochemical analysis methods such as these for analytical definition of chemical and biochemical substances are characterized by high sensitivity as well as high selectivity. However, while complex, expensive and sensitive optical and optoelectronic appliances are required for optical analysis methods, electrochemical analysis methods require only comparatively simple electrode apparatuses. One major advantage of electrochemical analysis methods is the direct presence of the measurement result in the form of an electrical signal. This can be processed further, after analog/digital conversion, directly by a computer, preferably by a personal computer.

Electrochemical analysis methods are suitable for qualitative and quantitative measurement of substance concentrations in an electrolyte solution. Each substance has an oxidation voltage or reduction voltage which is characteristic of it. These voltages can be used to distinguish between different substances. Furthermore, the concentration of the substance under consideration can be deduced from the electric current which flows during a reaction.

An electrochemical experiment requires at least two electrodes which are connected (working electrode, opposing electrode) to the substance (electrolyte) to be analyzed. However, a plurality of working electrodes can also be used in parallel. A reference electrode is generally also used in order to exactly monitor the electrolyte potential. This system, which has at least three electrodes, is connected to a potentiostat, which allows regulation of the potential at the working electrode and measures the electric current flowing through the working electrode.

In the case of voltammetry, a variable voltage is applied to the working electrode and the current flowing during oxidation or reduction is measured. In the specific case of cyclic voltammetry, a specific voltage range is covered repeatedly in such a manner that the substances contained in the electrolyte are oxidized and reduced a plurality of times successively.

In the case of chronoamperometry, a defined voltage is applied suddenly to the working electrode, and the current flowing is recorded over time. This measurement method allows the analysis of one specific substance by deliberate oxidation or reduction of this substance. The current flowing is a measure of the amount of substance converted per unit time, and allows conclusions to be drawn about the concentration of the substance and of the diffusion constants.

Chronocoulometry corresponds to chronoamperometry, in terms of the electrical constraints. However, in contrast to this, the total amount of electrical charge that has flowed is recorded rather than the electric current flowing.

In the refinement as sensors, electrode apparatuses can be used in different electrochemical analysis methods. The only critical factor is that substances which can be evaluated electrochemically are produced when a sensor event occurs. For example, a marking method which produces electrochemical substances when a sensor event occurs is used for sensors for detection of biomolecules.

Miniaturized electrochemical electrode systems for analysis of chemical and biochemical substances are known in the prior art [1], [2], [3], [4] and [5]. The electrodes of arrays such as these can be made contact with individually at the edge of the substrate, and can be operated by means of a potentiostat. In order additionally to provide electrode arrays which, for example, have 100 or more electrodes, switching functions on the substrate are advantageous, which multiplex the electrodes onto common connecting lines. If the substrate is a semiconductor material such as silicon, the switches required can be provided by MOS transistors, as described in [6]. Since the tests can in this case be carried out in parallel, the analysis time is considerably shortened, and it is also possible to carry out complex analyses.

Reference [7] describes the so-called EDDA method (Electrically Detected Displacement Assay Method), from the Friz BIOCHEM™ Company.

From the point of view of miniaturization, signal integrity and measurement sensitivity, the active micro arrays which are known from the prior art represent very good electrochemical analysis systems [2]. In this case, not only the multiplexing and/or selection functions but also the amplification, the conditioning of the signals and, possibly, also the evaluation of the signals are integrated in the semiconductor material. These sensor arrays are referred to as active arrays since, in contrast to passive arrays, active electronics process signals on the chip. Active electrochemical sensor arrays such as these, which operate using voltammetric (chrono)amperometric and (chrono)coulometric methods are manufactured using CMOS technology and are equipped with electrodes which are accessible on the chip surface and are composed of a noble metal (for example gold).

By way of example, active sensor arrays have been implemented for DNA sensor chips, in which redox cycling is used as the basis for verification of DNA molecules on surfaces electronically by detection of electrical charge carriers that are produced by means of redox-active substances. Redox cycling represents a special case of an amperometric method (oxidation/reduction voltages constant, measurement of the electrode current).

A typical redox cycling sensor arrangement has two gold electrodes formed on a substrate. By way of example, immobilized single-strand DNA capture molecules with a predetermined sequence are immobilized on each electrode by means of so-called gold-silver coupling. The complementary single-strand DNA target molecules which may be present in the analyte solution and thus have the capability for hybridization have a marking.

When suitable additional molecules are present, this marking is used to initiate a cycle comprising oxidation and reduction of components of the additional molecules, leading to the formation of reduced or oxidized molecules by interaction with the electrodes. The cycle comprising oxidation and reduction processes leads to an electrical circulating current which allows verification of the DNA target molecules.

The opposing electrode is always required both for this redox cycling sensor arrangement and for the already mentioned electrochemical analysis methods. However, while only a relatively small direct current need be dissipated to the electrodes in the case of redox cycling sensors, a comparatively high surge current must be able to be supplied by the opposing electrode in most of the electrochemical analysis methods mentioned above. For this reason, the area of the opposing electrode must be considerably larger than that of the active working electrodes.

Depending on the specific analysis method, the opposing electrode generally needs to have a surface area which is about 10 times larger than the sum of the surface areas of the individual working electrodes. This is necessary because, if the area of the opposing electrode is too small, the voltage which is applied to it can assume extremely high values in order to produce the charge carriers that are required for an experiment. When high values such as these are assumed, this can result in chemical reactions taking place in an uncontrolled manner, for example with the electrode material, and these typically lead to the formation of gases.

If the surface area of the opposing electrode is large enough, it is able to stabilize the electrolyte potential most of the time, by way of the double-layer capacitance. Electrochemical reactions take place only with comparatively low current densities.

Since an active silicon chip is comparatively expensive as a substrate, for example for a DNA sensor, it is generally desirable for the individual sensors in the array to be packed as densely as possible. In some circumstances, the packing density of the sensors and thus of the electrodes in the area of the sensor array can mean that it is not possible to provide an opposing electrode. The opposing electrode can then be in the form of an external electrode, which is arranged in the sample volume and is electrically connected to the sensor chip. This electrode can be driven from a potentiostat.

However, this procedure is disadvantageous because of the comparatively long supply lines and the more complex mechanical design. If the disadvantages associated with this are intended to be avoided, the only solution available from the prior art is for the opposing electrode to be formed in the periphery of the array, but this results in additional (expensive) chip area being required.

Reference [8] describes an electrode system for detection of molecules or molecule complexes. The arrangement according to [8] contains three electrodes, specifically a working electrode, an opposing electrode and a reference electrode. The reference electrode is arranged in such a manner that it is adjacent to at least subareas of the two further electrodes. Evaluation circuits are integrated in the substrate, with the working electrode and the electrode pair comprising the opposing electrode and the reference electrode being firmly connected to evaluation circuits, which are separate from one another.

Reference [9] describes a circuit for switching between different electrodes in an electrolysis apparatus. The electrolysis apparatus has an auxiliary electrode, a reference electrode, two working electrodes and a separation electrode. In a first working phase, a first working electrode is connected to a potentiostat, while the second working electrode is connected to the separation electrode. An electrolyte is deposited in a reference solution on the separation electrode. In a second working phase, the electrolyte which has been deposited on the separation electrode is separated from it, and a current which occurs during this process is measured.

Reference [10] describes a DNA sensor having interdigital electrodes. The interdigital electrodes have additional reaction surfaces for the accumulation of thiols.

Furthermore, [11] describes a biosensor having three electrodes, with the first electrode having a holding area for holding capture molecules. The second electrode and the third electrode are designed in such a manner that a redox process takes place on them in the course of a redox cycling process.

Furthermore, [12] describes a biosensor having a unit for immobilization of biopolymers. Furthermore, a detection unit is provided for detection of biopolymers, which are bonded to capture molecules which are applied to the unit for the immobilization of biopolymers, as well as a thermostatization unit which is designed to separate complexes comprising capture molecules and detected biopolymers by raising the temperature to a temperature above the melting point of the complexes.

References [13] and [14] describe methods for detection of biopolymers, in which capture molecules which have not been hybridized are removed from biopolymers with capture molecules using a hybridization process, and the hybridized biopolymers are detected after the removal process.

SUMMARY

At least one embodiment of the invention is based in particular on the problem of provision of a sensor array as well as a method for operation of a sensor array, in which the problems that are known from the prior art relating to the provision of an opposing electrode are reduced.

The problem is reduced or even solved by a sensor array of at least one embodiment and/or by a method for operation of a sensor array of at least one embodiment.

The sensor array according to at least one embodiment of the invention has at least three electrodes and one switching unit, wherein the at least three electrodes can be selectively connected via the switching unit as an opposing electrode or as a working electrode which can be electrically coupled to an electrolytic analyte, and wherein the at least three electrodes are designed in such a manner that sensor events take place at one electrode, which is connected as a working electrode, of the at least three electrodes in the electrolyte solution when in the presence of the electrolytic analyte.

The provision of a switching unit results in the deactivation of the operating circuit for the electrode that is acting as the sensor electrode, and the production of a connection between the electrode and the opposing electrode connection of a potentiostat.

The electrode of a sensor arrangement is designed in such a manner that sensor events take place on the electrode that is connected as the working electrode, in the presence of the electrolytic analyte to be verified. The opposing electrode of the overall system, that is to say of the sensor array, is provided by interconnection of the electrodes which are connected to the opposing electrode connection of the potentiostat, and whose operating circuits as sensor electrodes have been deactivated.

This allows the opposing electrode that is required for electrochemical experiments to be provided by interconnection of unused sensor electrodes in a sensor array. There is therefore no need for any separate opposing electrode, which occupies a large area, and monolithically integrated electrochemical analysis systems, in particular, can be produced more cost-effectively since there is no need to provide expensive chip area for the provision of an opposing electrode.

The expression a working electrode means in particular an electrode which is coupled to an electrolytic analyte and on which electrochemical reactions, for example, take place which are relevant for a sensor event.

The expression an opposing electrode means, in particular, an electrode which is coupled to an electrolytic analyte and provides electrical charge carriers as required for it, in order to set a predetermined electrochemical potential of the analyte.

The operating circuit, which is coupled to the electrode when connected as the working electrode, is preferably designed in such a manner that it produces an electrical sensor signal which characterizes sensor events when such sensor events occur. By way of example, this sensor signal may be a sensor current or a sensor voltage. The sensor signal can also be preprocessed on-chip, for example by being digitized and/or amplified, in order to improve the signal-to-noise ratio.

It is also preferable for the sensor array, according to at least one embodiment of the invention to be designed in such a manner that the individual sensor electrodes are monolithically integrated in and/or on a substrate. By way of example, the substrate may be a semiconductor substrate, in particular a silicon substrate (such as a silicon wafer or a silicon chip). This allows miniaturized integrated circuits to be used to drive the sensor electrodes. The circuit element or elements for an electrode, for example the operating circuit, can be provided with the electrodes underneath the electrochemical system, thus allowing a particularly space-saving configuration. Alternatively, at least a first portion of the components of the circuit can be provided externally (that is to say separately) from a substrate, in and/or on which a second portion of the components of the sensor arrangement is formed.

The circuits for driving the electrodes in the sensor array according to at least one embodiment of the invention must be designed in such a manner that the operating surface for the sensor electrode can be deactivated. In this context, can be deactivated means that, when in the inactive state, no charge carriers can flow from the operating circuit to the working electrode. This can be achieved either by means of complete decoupling of the electrode by means of a switch (switching transistor, transmission gate) or by the choice of a suitable operating point for the working electrode circuit, which satisfies the above requirement. Furthermore, the sensor electrode must be connected within the sensor array to a switching unit which makes the connection between the electrode and the opposing electrode connection of the potentiostat. This switching unit preferably has at least one MOS transistor.

According to another aspect of at least one embodiment of the invention, which can be implemented independently of the invention described above, a monolithically integrated sensor arrangement is provided having a plurality of electrodes, having at least one opposing electrode, at least one reference electrode as well as at least one working electrode, an operating circuit, which is coupled to the working electrode, for driving the working electrode, as well as a potentiostat circuit for provision of a predetermined potential.

In contrast to the prior art, according to which the potentiostat circuit is arranged externally to the electrode arrangement, and is connected to it by way of cables, the potentiostat circuit according to this aspect of the invention is monolithically integrated in the sensor arrangement.

According to at least one embodiment of the invention, the interference (which is caused by the so-called antenna effect and occurs as a result of the relatively long electrical supply lines (cables) which are present according to the prior art) of the relatively small electric currents which occur in the sensor and are to be detected is considerably reduced in this way. This considerably increases the resolution that can be achieved by means of the sensor arrangement according to this aspect of at least one embodiment of the invention, and the signal bandwidth which can be processed. Furthermore, according to this aspect of at least one embodiment of the invention, a greater number of electrode systems (that is to say in each case at least one opposing electrode, at least one reference electrode as well as at least one working electrode) can be operated at the same time.

Furthermore, the monolithically integrated sensor arrangement may have one or more digital control devices and/or analog control devices for controlling the electrode system or systems, preferably as well as peripheral circuits which are likewise all integrated in the sensor arrangement.

Furthermore, the measurement electronics for detection and processing of the electrical signals from the operating circuits of the working electrodes are preferably likewise integrated in the monolithically integrated sensor arrangement.

According to one refinement of this aspect of at least one embodiment of the invention, the potentiostat circuit is designed and is coupled to the opposing electrode in such a manner that the predetermined potential is produced as a constant potential of the electrolyte (constant electrolyte potential). The voltage change which is required during sensor operation is produced by the operating circuit, and is supplied to the working electrode.

In this electrochemical method, in which the electrolyte potential is kept essentially constant with respect to the supply voltage of the electronic chip, the potentiostat circuit always operates at the same operating point, that is to say it compares the electrolyte voltage which is provided for it from the reference electrode with a fixed predetermined reference voltage, and drives the opposing electrode in such a manner that the electrolyte potential remains essentially constant. The working electrode voltage change which is required in all of the electrochemical experiments that have been mentioned is in this case ensured by the operating circuit, which is coupled to the working electrode.

The operating circuit, or if appropriate the plurality of operating circuits, receives or receive a voltage which varies over time for the working electrodes, and regulates the electrical current flow from and to the working electrode or electrodes in such a manner that the electrical voltage at the working electrode or the working electrodes follows this voltage. The electric current that flows represents the measurement signal, and is used for evaluation of the electrochemical reactions at the working electrode or at the working electrodes. The potentiostat circuit operates autonomously and stabilizes the bath potential, that is to say the electrical potential in the electrolyte, at the reference potential. This procedure is particularly advantageous when different electrical potentials have to be applied to a plurality of different working electrodes which are accommodated in a common reaction volume.

For voltammetry purposes, a continuously varying electrical voltage is applied to the working electrode, and the electric current that flows is measured. If the electrical voltage is varied repeatedly between two limit values, then this is referred to as cyclic voltammetry. The electric current which flows to the working electrode or to the working electrodes is detected and processed further by suitable measurement electronics.

For chronoamperometry purposes, the electrical potential is applied suddenly to the working electrode at a specific predetermined level and the changes in the electrode current over time which result from the oxidation processes and/or reduction processes that take place are measured.

For chronocoulometry purposes, the electrical charge flowing to the working electrode is measured rather than the electrode current. This can be done on the one hand by integration of the electrode current in an analog integrator circuit, that is to say by use of a capacitor, or by deliberate transfer of charge packets (charge pumping) or by digitization of the electrode current followed by digital integration.

According to another refinement of this aspect of at least one embodiment of the invention, the potentiostat circuit is designed and is coupled to the opposing electrode in such a manner that a first input of the potentiostat circuit is supplied with the instantaneous electrical potential in the electrolyte, and in such a manner that a second input of the potentiostat circuit is supplied with the voltage change that is required for sensor operation, as an electrical voltage which varies over time, so that the electrical potential which is applied to the opposing electrode varies over time. The operating circuit produces an electrical potential and supplies this to the working electrode in such a manner that the electrical potential which is applied to the working electrode is kept essentially constant over time.

In this electrochemical method, in which the electrical potential at the working electrode is kept essentially constant with respect to the supply voltages of the electronic chip in which the monolithically integrated sensor arrangement is integrated, the electrical potential at the working electrodes is kept constant, and the electrical potential of the electrolyte is varied.

This is of particular interest for the situation in which all of the working electrodes in a reaction volume must have the same effective oxidation voltage or reduction voltage. This refinement is therefore particularly suitable for relatively large sensor arrangements having a large number of sensor arrays, in which each individual sensor verifies the concentration of one specific electrochemical active substance, which is the same for all the sensors, that is to say this requirement is particularly suitable for electrical DNA sensors.

According to at least one embodiment of this refinement, the desired bath voltage, which varies over time, that is to say the voltage of the electrolyte, is applied to one input of the potentiostat circuit, and is compared with the electrical potential of the reference electrode. The desired bath voltage, which varies over time, is set via the opposing electrode, by means of the potentiostat circuit. The working electrode circuits, that is to say the operating circuits, keep the working electrodes or the working electrode at an essentially constant electrical potential, and measure the current or the amount of charge that is required for this purpose.

The separation of the apparatus for voltage variation (that is to say the potentiostat circuit) and the apparatus for current measurement or charge measurement (that is to say the operating circuit) considerably simplifies the circuit design.

Particularly for experiments in which a step-function voltage change is carried out, the architecture described above has considerable advantages in terms of the time response and the stability of the sensor arrangement.

For voltammetry purposes, a continuously varying voltage is applied to the potentiostat, that is to say to the potentiostat circuit. The electrolyte follows this voltage change as a result of the corresponding drive to the opposing electrode by way of the potentiostat circuit, and the electric current which flows is measured at the working electrodes. If the electrical voltage is repeatedly varied between two limit values, then this procedure is referred to as cyclic voltammetry. The electric current which flows at the working electrode is detected and processed further by suitable measurement electronics, which may likewise be integrated in the sensor arrangement.

For chronoamperometry purposes, the potential of the potentiostat circuit suddenly has a predetermined specific level applied to it, and the electric current, which varies over time as a result of the oxidation processes and/or reduction processes that take place, is measured at the working electrode.

For chronocoulometry purposes, the electrical charge flowing to the working electrode is measured rather than the electrode current. This can be done on the one hand by integration of the electrode current in an analog integrator circuit (that is to say by means of a capacitor), or by deliberate transfer of charge packets (charge pumping), or by digitization of the electrode current followed by digital integration.

Particularly if the electrodes have very small surface areas, it is advantageous to keep the working electrodes at a constant electrical potential with respect to the operating voltage of the electronic chip, and to vary the electrolyte voltage. In this case, the parasitic input capacitance of the operating circuit for the working electrodes remains at a constant electrical potential, and its charge does not change when a step-function voltage change occurs. The parasitic input capacitance which, in the case of small electrodes, is in the same order of magnitude as the double-layer capacitance of the electrode itself, in this case does not lead to any corruption of the measurement result.

Alternatively, the operating circuit of the sensor electrodes which are connected as the opposing electrode can also be driven in such a manner that the electrode potential follows the potential at the opposing electrode connection of the potentiostat. In this case, it is not absolutely essential to provide a switch in the sensor pixel. The switching unit may also have a switch which is located at the edge of the matrix and drives a plurality of sensor pixels, for example all of the sensor pixels in one column.

The sensor array according to at least one embodiment of the invention is preferably designed in such a manner that it has a control circuit which is designed to drive, select and/or read the sensor electrodes or some of the sensor electrodes (for example the electrodes in one row or column of sensor pixels). A control circuit such as this, which can be integrated on and/or in a chip or can be provided externally from the chip, contains, for example, a large number of selection transistors, word lines and column lines, in order to drive or to select individual sensor pixels deliberately, or to read a sensor signal.

The electrodes in the sensor array according to at least one embodiment of the invention can be designed to detect substances which can be oxidized or reduced. These sensor arrays may have 50 to 1 000 000, preferably 100 to 250 000, individual sensor electrodes. In the sensor array according to at least one embodiment of the invention, the sensor pixels can be arranged essentially in the form of a matrix, that is to say in rows and columns. This allows a particularly high integration density for the sensor pixels, and this is advantageous in particular for high throughput analyses, in which each sensor electrode is sensitive to a different biomolecule, for example to oligonucleotides with a different base sequence.

One example embodiment of the invention relates to a sensor array in which the electrodes are designed to detect biomolecules. These biomolecules are, for example, nucleic acid molecules, peptides and/or proteins. The electrodes within the sensor array are preferably designed in such a manner that capture molecules are immobilized on the surface of the electrodes. These capture molecules are able to identify the biomolecules to be detected, and to specifically bind to them.

By way of example, electrodes can be functionalized for analysis of DNA molecules by the immobilization of single-strand DNA fragments, which are complementary to the DNA molecules to be detected and thus have the capability for specific hybridization. If required, a functionalized layer such as this can also provide the electrochemical markings for the subsequent detection process.

It is preferable for the immobilized capture molecules to have ferrocene markings. The detection principle on which this marking is based is based on the oxidation of ferrocene markings (oxidative step-function voltage change), in which the working electrode is changed to a suitable positive potential with respect to the potential of the electrolyte. The amount of electrical charge which flows when the step-function voltage change occurs is a direct measure of the amount of ferrocene which is present at the relevant electrode.

A sensor signal can be generated in the sensor array according to at least one embodiment of the invention by means of electrochemically active markings in the presence of an electrolytic analyte. The electrochemically active markings may have metal-complex markings. The electrochemically active markings may have ferrocene markings. Electrochemically active markings such as these may be applied to capture molecules, target molecules, intercalators or signal oligomers.

If, according to at least one embodiment of the invention, an electrode such as this is now also used as an opposing electrode, then it is necessary to ensure that the functionalization is not destroyed by this. This is ensured if the total area of the sensor electrodes which are connected as an opposing electrode is considerably greater than the area of the active sensor electrodes. In this case, the voltage at the opposing electrode does not assume extreme values.

It is thus preferable for the electrodes in the sensor array which are interconnected as the opposing electrode to have, overall, approximately 10-times to 100-times the area of the electrode or electrodes which is or are connected as the working electrode or electrodes. This is preferable because, in this case, a potential shift of the electrolyte essentially takes place to the capacitive coupling of the opposing electrode to the electrolyte via the double-layer capacitance, and only a negligibly small number of reactions take place at the opposing electrode. The voltage change which a potentiostat causes at the opposing electrode in this case has a negligibly small amplitude.

In the case of oxidation of ferrocene markings, the opposing electrode becomes slightly negatively polarized with respect to the electrolyte when a step-function voltage change occurs. The ferrocene molecules which are immobilized there can thus in consequence not be oxidized. Markings which have already been oxidized are reduced again in these circumstances. In any case, the functionalization of the sensor electrodes which are used as the opposing electrode remains intact. The same applies in a corresponding manner to the situation in which markings which are detected by means of a reductive step-function voltage change are present on the electrode surface.

Furthermore, the sensor electrodes of the sensor array according to at least one embodiment of the invention may be in the form of dynamic biosensor arrangements. The expression a dynamic biosensor arrangement means in particular a biosensor arrangement such as this which is operated not only effectively in the steady state but in which dynamic measurement signals occur, that is to say measurement signals which vary greatly over time (for example step-function voltage changes, AC voltage voltammetry, etc.).

A further subject matter of the invention is a method for operation of the sensor array described above in an electrochemical analysis method.

In a first step of the method according to the an embodiment of invention, a first number of the at least three electrodes, which number comprises at least two electrodes, are first of all interconnected, are connected to the opposing electrode connection of a potentiostat, thus forming the opposing electrode for the overall system. At the same time, a second number of the at least three electrodes, which number comprises at least one electrode, is connected as a working electrode or working electrodes for detection of an electrolytic analyte.

In a further step, once the sensor events have been detected at the stated electrodes which are connected as working electrodes, at least one of the electrodes which was previously connected as the opposing electrode is disconnected from the opposing electrode connection of the potentiostat, and is connected as a working electrode. At the same time, the operating circuit for at least one electrode which was connected as a working electrode in the first step is deactivated, and, as part of the opposing electrode of the sensor array, is connected to the opposing electrode connection of the potentiostat.

The sequence of the method steps mentioned above, that is to say the change between the connection of an electrode of the sensor array as a working electrode and as an opposing electrode and vice versa, can be repeated as often as desired.

Overall, the method according to an embodiment of the invention provides the capability for the individual working electrodes in the sensor array to be driven actively and flexibly. Since the sensor (working) electrodes which are provided in the sensor array cannot all be used as electrodes for detection of the analyte at the same time, the rest of the electrodes can be connected jointly as an opposing electrode.

This procedure allows the requirement for a large-area opposing electrode to be complied with easily. In any case, the sensor pixels are normally read only successively, so that there is no need for simultaneous operation as a working electrode. For example, the sensors in one row or in one column of the sensor array can thus be used as active sensors. All of the other sensor electrodes can operate in an interconnected form as the opposing electrode for the overall system. It is also obvious to a person skilled in the art that sensors in the sensor array which are selected randomly or irregularly can also be deactivated with respect to their operating circuit, and then only these electrodes can act as the opposing electrode.

The method according to an embodiment of the invention is independent of the form of the respective electrodes. These are preferably flat. However, segmented electrodes are also suitable. The process of interconnection of the electrodes which are not activated as sensor electrodes is preferably carried out to such an extent that the overall surface area of the electrodes which are connected as opposing electrodes is at least 10-times as great as the overall surface area of the electrodes which are connected as working electrodes.

It is also preferable in the method according to an embodiment of the invention for operation of a sensor array in an electrochemical analysis methods to be used in which at least one substance in an electrolyte is defined qualitatively and/or quantitatively on the basis of its characteristic oxidation voltage or reduction voltage by way of voltammetry, amperometry and/or coulometry.

The method according to an embodiment of the invention can preferably be used for analysis of biomolecules. For this purpose, by way of example, the electrodes can be provided with immobilized ferrocene-marked capture molecules, and the concentration of the biomolecules can be determined by measurement of the amount of charge flowing during oxidation of the ferrocene.

In principle, it is also possible, in addition to the use of the method according to an embodiment of the invention, to additionally equip the chip with a conventional opposing electrode. This can considerably improve the time response of the overall system.

In the method according to an embodiment of the invention, the operating circuit of a working electrode is deactivated before switching to operation as an opposing electrode, via a switching unit. Only some of the electrodes in the sensor array are connected as working electrodes for detection of the analyte. By way of example, only those sensors in one column of the sensor array are selected as active sensors which will carry out the measurement as described above. All of the other electrodes (for example all of the other columns) are in contrast connected to one another by means of suitable integrated switching transistors, and are made available to the potentiostat as an opposing electrode. These electrodes which act as an opposing electrode do not operate in the sensor mode, and no information relating to the sensor events is obtained from these sensor pixels.

One aspect of an embodiment of the invention can clearly be regarded as being the provision of a monolithically integrated electrochemical analysis system for highly sensitive detection, with a high degree of parallelity, of electrochemically active species by way of voltammetry, chronoamperometry and/or chronocoulometry.

In particular, the method of an embodiment as described above for potentiostat operation, in which the working electrode potential is kept constant and, instead of this, the electrical potential of the electrolyte is varied, has considerable advantages in the situations described above.

Furthermore, the sensor arrangement according to an embodiment of the invention is highly advantageous for so-called step-function voltage change experiments by virtue of the suitable circuitry measures with the electrical circuits monolithically integrated in the sensor arrangement, in order to ensure the stability of the sensor arrangement during the sudden-voltage change experiment.

The monolithic integration of electrodes and operating circuit allows the production of high-density, highly sensitive sensor arrays while maintaining the high edge gradient that is required for step-function voltage change experiments.

BRIEF DESCRIPTION OF THE DRAWINGS

Example embodiments of the invention will be explained in more detail in the following text and are illustrated in the figures, in which:

FIG. 1 shows a schematic illustration of an arrangement of a large number of sensor pixels according to one aspect of an embodiment of the invention;

FIG. 2 shows a pixel circuit according to one aspect of an embodiment of the invention;

FIG. 3 shows a pixel circuit according to another aspect of an embodiment of the invention;

FIG. 4 shows a pixel circuit according to one aspect of an embodiment of the invention;

FIG. 5 shows a pixel circuit according to another aspect of an embodiment of the invention;

FIG. 6 shows the pixel circuit as shown in FIG. 4, illustrated in a simplified form;

FIGS. 7a and 7b show pixel circuits with reference circuits according to different aspects of an embodiment of the invention;

FIG. 8 shows a pixel circuit according to another aspect of an embodiment of the invention;

Identical or similar components in the various figures are provided with the same reference numbers.

Figure 7B:
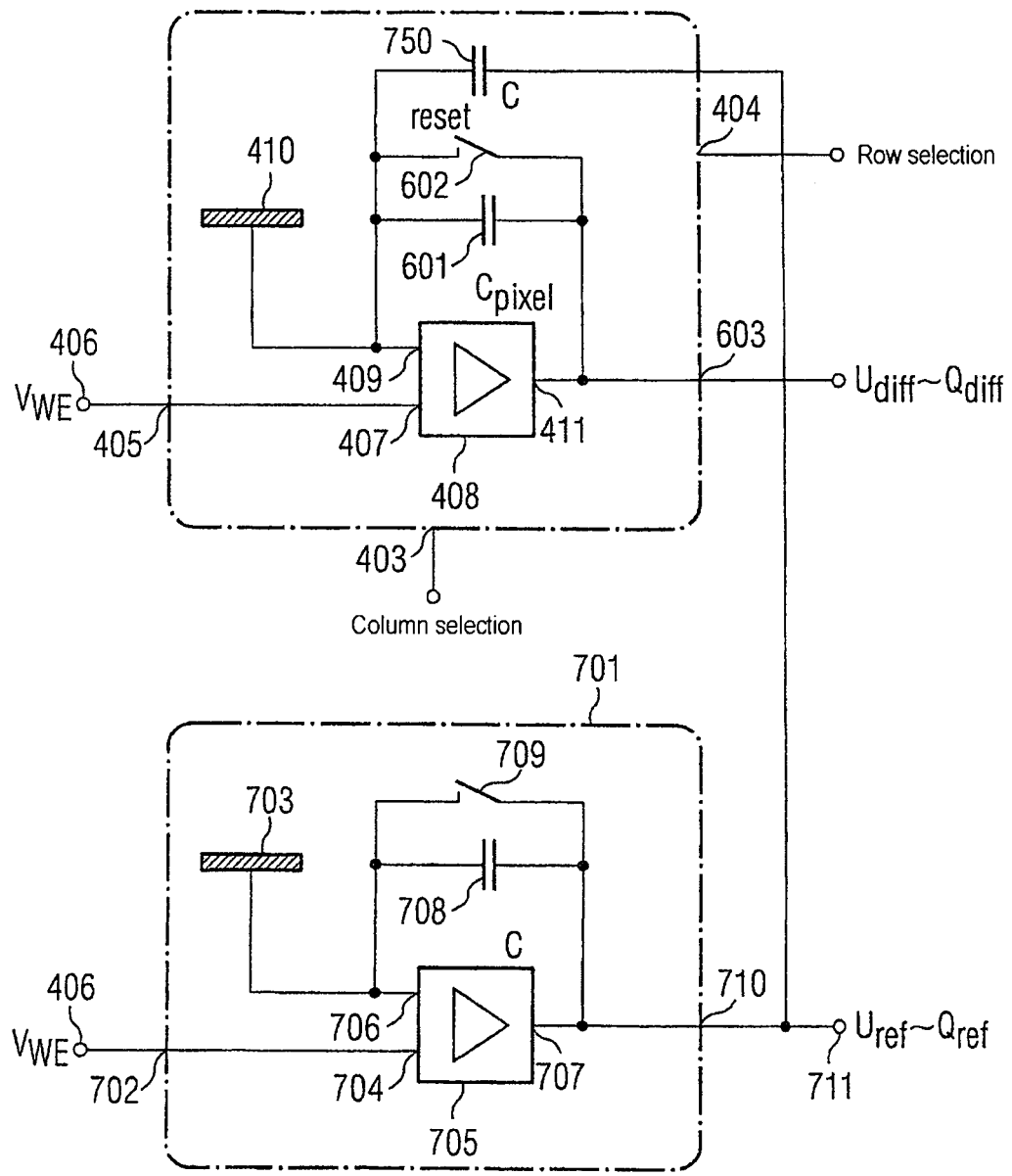

The illustrations in the figures are schematic and not to scale.

DETAILED DESCRIPTION OF THE EXAMPLE EMBODIMENTS

The pixel arrangement illustrated in FIG. 1 shows, by way of example, the selection of the sensors in one column 101 as active sensors, while the electrodes in all of the other sensor arrangements 102 (all of the other columns) are connected, for example, by way of suitable integrated switching transistors, and are made available as an opposing electrode to the potentiostat. The potentiostat circuit can be designed and coupled to the opposing electrode in such a manner that the predetermined potential is produced as a constant electrolyte potential. The potentiostat circuit compares the electrolyte voltage, which is made available to it from the reference electrode (RE) with a fixed predetermined reference voltage, and drives the opposing electrode in such a manner that the electrolyte potential remains essentially constant.

FIG. 2 shows a pixel circuit 200 according to one embodiment of the invention, in which the switching element which makes the connection between the electrode and the opposing electrode connection of the potentiostat is formed within the sensor pixel. Each pixel circuit is electrically coupled to the respective working electrode for detection of the sensor event that occurs at the working electrode. The column selection input 203 is coupled to the column control from FIG. 1. The column selection signal is supplied to the pixel circuit 200 via the column selection input 203. A second input 204, also referred to as a row selection input 204, is coupled to the row control shown in FIG. 1 and is used to supply the row selection signal to the pixel circuit 200. Furthermore, a third input 205 is provided for supplying a reference potential $V_{WE}$ 206 to a first input 207 of an operational amplifier 208, which is likewise provided in the pixel circuit 200. The second input 209 of the operational amplifier 208 is coupled to the working electrode 210 of the respective pixel circuit 200.

FIG. 3 shows an alternative pixel circuit 300 according to a further embodiment of the invention. This type of circuit for an electrode in the sensor array has no switch in the sensor pixel and, instead of this, has a switching unit, which has at least one switch, at the edge of the matrix, which drives a plurality of pixels, for example all of the pixels in one column.

The pixel circuits described in the following text are each arranged underneath a sensor electrode, for example as is illustrated in FIG. 1, and are monolithically integrated in the silicon material, so that each of the circuit components which are described in the following text are formed and are connected to one another so as to ensure the functionalities described in the following text.

The sensor arrangements described in the following text are in the form of DNA sensors for detection of macromolecular biopolymers, with an electrochemical detection process being used for detection of the macromolecular biopolymers according to these exemplary embodiments of the invention, in which a hybridization event is verified indirectly by means of signal-emitting electrochemical markings on the capture molecule, on the target molecule, on signal oligomers and by intercalators. In particular, intercalators are substances which become incorporated on or in double-strand DNA selectively. This makes it possible to discriminate between individual strands and double strands.

According to the method described in [7], short-strand signal oligomers are hybridized with the capture molecules (sample molecules) that are immobilized on the working electrodes. The substance to be analyzed is then brought into contact with the electronic chip, and any target molecules whose sequence is complementary to the respective sample molecules, also referred to as capture molecules, which are present displace the short-strand signal oligomers in the substance to be analyzed. Ferrocene molecules are normally applied to the signal oligomers as a marking. The electrochemical system then detects the presence of the ferrocene molecules at the various sensor positions.

In this context, it should be noted that the sensor arrangements described in the following text are suitable for all types of electrochemical experiments in which content substances of the electrolyte or of substances which have been immobilized on the electrode surface are oxidized and/or reduced.

The following embodiments thus describe a DNA analysis system for chronoamperometry and chronocoulometry which is generally able to provide a step-function voltage change of several 100 mV (typically 400 mV) within a time interval of less than one microsecond, or else in principle any desired longer time intervals, on the respective working electrode.

Owing to the time requirements described above, it is actually impossible to use a macroscopic potentiostat circuit for very small electrode areas, that is to say for electrodes with a very small surface area, since wiring capacitances and appliance capacitances do not allow the necessary signal bandwidth. Since, in the DNA analysis system according to an embodiment of the invention and described in the following text, the operating circuits are arranged in a pixel directly underneath the electrode, the parasitic capacitance which has to drive the working electrode is considerably reduced, and very short step-function change times can be achieved.

Short step-function change times are required since, in this case, it is easily possible to distinguish between electrochemically active substances which are directly present on the electrode and diffuse contributions to the oxidation current or to the reduction current. The substances which are directly present on the respective electrode are oxidized or reduced within a very short time, while the free substances which are present in the analyte can contribute to the signal current considerably later, because of their specific diffusion constants.

In a step-function voltage change experiment, the current at the working electrode is essentially split into three contributions:

Changing charge on the double-layer capacitance:
  The double-layer capacitance must always be taken into account when a conductive electrode is in contact with an electrolyte. Ions are essentially arranged in two layers in the immediate vicinity of the electrode surface. This layer system can be regarded as an (electrolytic) capacitor, in which the two capacitor plates are separated from one another by only a few molecules. This fact results in the (electrolytic) capacitor having extraordinarily high capacitance per unit area values. Values of 0.1 $F/m^2$ are typically achieved.
  With regard to the DNA sensor according to an embodiment of the invention, it is evident that the amount of charge which flows into the double-layer capacitance is in the same order of magnitude as the amount of charge which is applied for oxidation of the ferrocene.

Oxidation of the ferrocene:
  The ferrocene which is present on the electrode surface is oxidized directly in the event of an effectively positive step-function voltage change at the working electrode. Since hybridized molecules are at most only a few nanometers away from the surface, these molecules are oxidized virtually completely within the step-function change time of the voltage. Thus, for measurement purposes, this current contribution is superimposed directly on the charging current for the double-layer capacitance.

Oxidation of diffusing ferrocene molecules:
  There is a significant concentration of ferrocene molecules in the analyte, including those which have been displaced by the capture molecules. These molecules diffuse out of the solution to the electrode and lead to an electric current flow which decays slowly after the step-function voltage change.

In this case, the primary measurement signal is the current flowing at the electrode during the step-function voltage change. However, the variable that is relevant for measurement purposes is the amount of charge which is required to stabilize the electrode voltage. This amount of charge is a direct measure of the absolute amount of ferrocene which has been oxidized. An integrator is preferably provided for this situation in the sensor arrangement, and integrates the respective electrode current.

As is shown in the pixel circuit 400 in FIG. 4, the respective integrator 401, 402 is contained directly in a respective sensor pixel. The pixel circuits described in the following text should in each case be understood on the basis that each pixel circuit is arranged physically underneath or in the immediate vicinity of a respective working electrode, as is shown in FIG. 1, and is electrically coupled to it in order to detect the sensor events which in each case occur at the working electrode.

The pixel circuit 400 shown in FIG. 4 has three inputs 403, 404, 405 as well as two outputs 416, 417 in addition to an oxidation integrator 401 and a reduction integrator 402.

A first input 403, also referred to as a column selection input, is coupled to the column control shown in FIG. 1. The column selection signal is supplied to the pixel circuit 400 via the column selection input 403.

A second input 404, also referred to as a row selection input 404, is coupled to the row control shown in FIG. 1 and is used to supply the row selection signal to the pixel circuit 400.

Furthermore, a third input 405 is provided for supplying a reference potential $V_{WE}$ 406 to a first input 407 of an operational amplifier 408, which is likewise provided in the pixel circuit 400. The second input 409 of the operational amplifier 408 is coupled to the working electrode 410 of the respective pixel circuit 400.

The output 411 of the operational amplifier 408 is coupled to a control input 412 in order to vary the electrical resistance of a first variable electrical resistor 413, one of whose connections is coupled to the input of the oxidation integrator 401 and whose other connection is coupled to the second input 409 of the operational amplifier 408 and to the working electrode 410, and is coupled to a first connection of a second variable resistor 414 whose second connection is coupled to the input of the reduction integrator 402. The control connection 415 of the second variable resistor 414 is likewise coupled to the output 411 of the operational amplifier 408. The output of the oxidation integrator 401 is coupled to a first output 416 of the pixel circuit 400, and the output of the reduction integrator 402 is coupled to a second output 417 of the pixel circuit 400. The electrode current 418 flowing through the working electrode is integrated by means of the integrators 401 and 402. The resultant electrical voltage $U_{ox}$ at the output of the oxidation integrator 401 and, respectively, $U_{red}$ at the output of the reduction integrator 402 is proportional to the respective amount of oxidation charge or amount of reduction charge as a variable which is relevant for measurement.

According to one alternative refinement, each of the integrators is provided outside the pixel circuit, as shown by way of example in the pixel circuit 500 in FIG. 5.

In the case of the pixel circuit 500 shown in FIG. 5 as well, the working electrode 501 is coupled to a first input 502 of an operational amplifier 503, whose second input 504 is coupled to a third input 505 of the pixel circuit 500, in order to supply the reference potential $V_{WE}$ 506.

The pixel circuit 500 also has a column selection input 507 as well as a row selection input 508, with the column selection input 507 being coupled to the column control unit, and with the row selection input 508 being coupled to the row control unit, as shown in FIG. 1.

The output 509 of the operational amplifier 503 is coupled to a control connection 510 of a first variable resistor 511, and to a control connection 512 of a second variable resistor 513.

The first variable resistor 511 is coupled by its first connection to one input of a first current-mirror circuit 514, whose output is coupled to a first output 515 of the pixel circuit 500. The second connection of the first variable resistor 511 is coupled to the working electrode 501 and to the second input 502 of the operational amplifier 503, as well as to a first connection of the second variable resistor 513, whose second connection is coupled to one input of a second current-mirror circuit 516, whose output is in turn coupled to a second output 517 of the pixel circuit 500.

The amplified electric current, which the first current-mirror circuit 514 multiplies by the current-mirror parameter n and which flows through the working electrode 501, is produced as an amplified oxidation current at the first output 515 and, depending on the switch position of a first switch 518, is produced directly for further processing as the first current output signal $I_{ox}$ 519 or is supplied to an oxidation integrator 520, which used the amplified oxidation current to form the oxidation voltage $U_{ox}$ 521, which is proportional to the amount of oxidation charge $Q_{ox}$.

An amplified reduction current is produced in a corresponding manner at the second output 517, multiplied by the factor n of the second current-mirror circuit 516 and, depending on the switch position of a second switch 522, is produced directly as a reduction output current $I_{red}$ 523 or to a reduction integrator 524, which produces a reduction output voltage $U_{red}$ 525 which is proportional to the amount of reduction charge $Q_{red}$.

In this case, the respectively active selective sensor, that is to say the respective selected pixel circuit 500 is connected by way of selection logic (represented in FIG. 5 by the symbolic switches 518 and 522) to the respective central integrator (oxidation integrator 520 or reduction integrator 524), and the correspondingly flowing current is measured.

If the pixel circuit contains the integrator, as is illustrated by way of example in the pixel circuit 600 in FIG. 6, then the pixel circuits 600 operate autonomously and, in principle, all the sensors in an array can be evaluated once.

The integrator results can be checked successively by means of suitable selection logic after the respective step-function voltage change experiment.

FIG. 6 shows a simplified illustration of the pixel circuit 400 as shown in FIG. 4, in which case the illustration shows only that the first input 407 of the operational amplifier 408 is coupled to the third input 405 of the pixel circuit 400, and that the working electrode is coupled to the second input 409 of the operational amplifier 408.

Furthermore, a feedback capacitor 601 is illustrated, whose first connection is coupled to the output 411 of the operational amplifier 408 and whose second connection is fed back to the second input 409 of the operational amplifier 408. A reset switch 602 is connected in parallel with the feedback capacitor 601 and is coupled on the one hand to the second input 409 of the operational amplifier 408, and on the other hand to the output 411 of the operational amplifier 408, which is coupled to the output 603 of the pixel circuit 600 and at which the output voltage signal, which is proportional to the amount of charge, is produced.

In particular, the working electrode circuit can be designed in such a manner that it is possible to compensate for the amount of charge from the double-layer capacitance, which carries no information as a result of functionalization. In this case, the sensor array has one electrode which is not functionalized, that is to say on which no capture molecules are immobilized and which thus exclusively measures the charge from the double-layer capacitance and the diffusive component.

The electric current which flows through this additional electrode during the step-function voltage change experiment, or the integrated electrical charge, can in each case be subtracted from the signals from the active sensors, so that these pixel circuits now supply only the charge signal or current signal that is relevant for measurement purposes.

FIG. 7a shows one such example embodiment in which the pixel circuit is in the form of the embodiment shown in FIG. 6.

As is illustrated in FIG. 7a, a reference circuit 701 is provided according to this embodiment, having an input 702 at which the reference potential $V_{WE}$ is produced. Furthermore, a reference working electrode 703 is provided, on which no capture molecules are immobilized, and which is provided with a coating which is not ready for binding.

The input 702 of the reference circuit 701 is coupled to a first input 704 of a reference operational amplifier 705, whose second input 706 is coupled to the reference working electrode 703. One output 707 of the reference operational amplifier is fed back via a reference capacitor 708 to the second input 706 of the reference operational amplifier 705 and, if required, is shorted via a reference reset switch 709 for resetting of the integrator to the second input 706 of the reference operational amplifier 705. One output 710 of the reference circuit 701 produces the integrated reference signal $U_{ref}$ 711. The difference between the output voltages from the two integrators, that is to say the difference between the output voltage produced by the pixel circuit 600 and the reference output voltage which is produced at the output 710 of the reference circuit, is used as the measurement signal for the electrochemical reactions at the working electrode 410 of the respective pixel.

The embodiment shown in FIG. 7*b* differs from the embodiment shown in FIG. 7*a* in that a central reference pixel is provided, which generates a central reference voltage signal $U_{ref}$ 711 which is fed back via a coupling capacitor 750 to all of the active sensor electrodes, and the double-layer capacitance and the diffusive reactions are exactly eliminated. The coupling capacitor 750 is connected between the output of the central reference circuit 701, whose design is identical to that of the reference circuit 701 shown in FIG. 13*a* and which is provided in each pixel, and the second input 409 of the respective operational amplifier 408 in the pixel circuit 600.

The output signal from the respective pixel circuit 600 thus now directly outputs only the signal of the electrochemical reactions, owing to the functionalization of the electrodes. This allows a very sensitive measurement of the amounts of charge that occur at the respective sensor, that is to say at the working electrode.

If the electrical charges which originate from the oxidation processes or the reduction processes occur at a considerably later time than the duration of the step-function voltage change, then the electrical charge carriers can be masked out from the charging of the double-layer capacitance for the delayed activation of the integrator.

The respective integrator is thus switched on or enabled in this case only when the voltage at the working electrode or at the working electrodes has reached the intended value and the electrochemical reactions which are relevant for measurement purposes are taking place.

As has been described above, the operating circuit for the working electrodes has the object of keeping the electrode potential constant and of measuring the current flowing through the working electrodes and/or the charge for an oxidative step-function voltage change and/or reductive step-function voltage change. A subtraction stage is provided for this purpose in the pixel circuit, which compares the electrode potential with a nominal potential and measures the current required to maintain the electrical voltage and/or stores the amount of charge. Since the electric current can assume very large/small values because of the rapid step-function voltage change with large/small electrodes, it is expedient to amplify or to divide the electrode current, before further processing by means of current-mirror circuits, in such a manner that the current assumes the normal values, which can be processed further by means of conventional digital circuits, for the integrated CMOS circuitry that is preferably used.

The current mirrors described in the embodiment thus have a division factor/gain factor of n. The output current from the current-mirror circuits is thus n-times the input current to the current-mirror circuits. n may be less than unity (for example 1/100, 1/10 for comparatively large electrodes) or greater than unity (10, 100 for comparatively small electrodes).

Two complementary current paths are required for measurement of oxidative signals and reductive signals, which can receive or supply the respective electrode current, for example as shown in the pixel circuit 500 in FIG. 5.

Normally, however, only one of the two electrochemical signals (oxidation/reduction) is relevant for measurement purposes, for which purpose only one branch is provided, as shown by way of example in the simplified illustration in FIG. 6. Thus, for simplicity and for miniaturization of the pixel circuits, one of the current branches in a pixel circuit can be formed by a single switch 800 (see FIG. 8), which, before the actual measurement, connects the working electrode 501 to the nominal potential, that is to say to the third input 505 of the pixel circuit 500, and dissipates to this voltage source any electric current which may be flowing.

It is also desirable for the operating circuit for the working electrodes to have a very wide dynamic range for the electrode current.

Very large electric currents occur briefly during the step-function voltage change (double-layer capacitance, oxidation signal). Both this large pulsed current and the subsequent small current resulting from further oxidation processes must be measured correctly by the operating circuit of the working electrodes.

Very precise current-mirror circuits are therefore desirable for this reason. High precision current-mirror circuits can be achieved by way of large-area current-mirror circuits in order that statistical fluctuations (resulting from the processes) of the component parameters of the current-mirror circuits do not exceed a specific value. Since large-area transistors which form a current-mirror circuit also have a high parasitic capacitance, the accuracy of the current-mirror circuit integrated in the pixel circuit would be restricted, since this capacitance must likewise be charged by the electrode current. The amount of charge does not appear, or appears only very late, at the output of the current-mirror circuit, and is thus not available for integration.

For high precision and a high measurement speed, it is expedient for the current-mirror units in the sensor pixel circuit to be precharged before the step-function voltage change. This can be done by means of a switching transistor 901 in a precharging unit 900 (see FIG. 9), which is coupled to the first current-mirror circuit 514, with the switching transistor 901 applying a suitable current to the first current-mirror circuit 514, and being switched off again shortly before the step-function voltage change.

Figure 9:
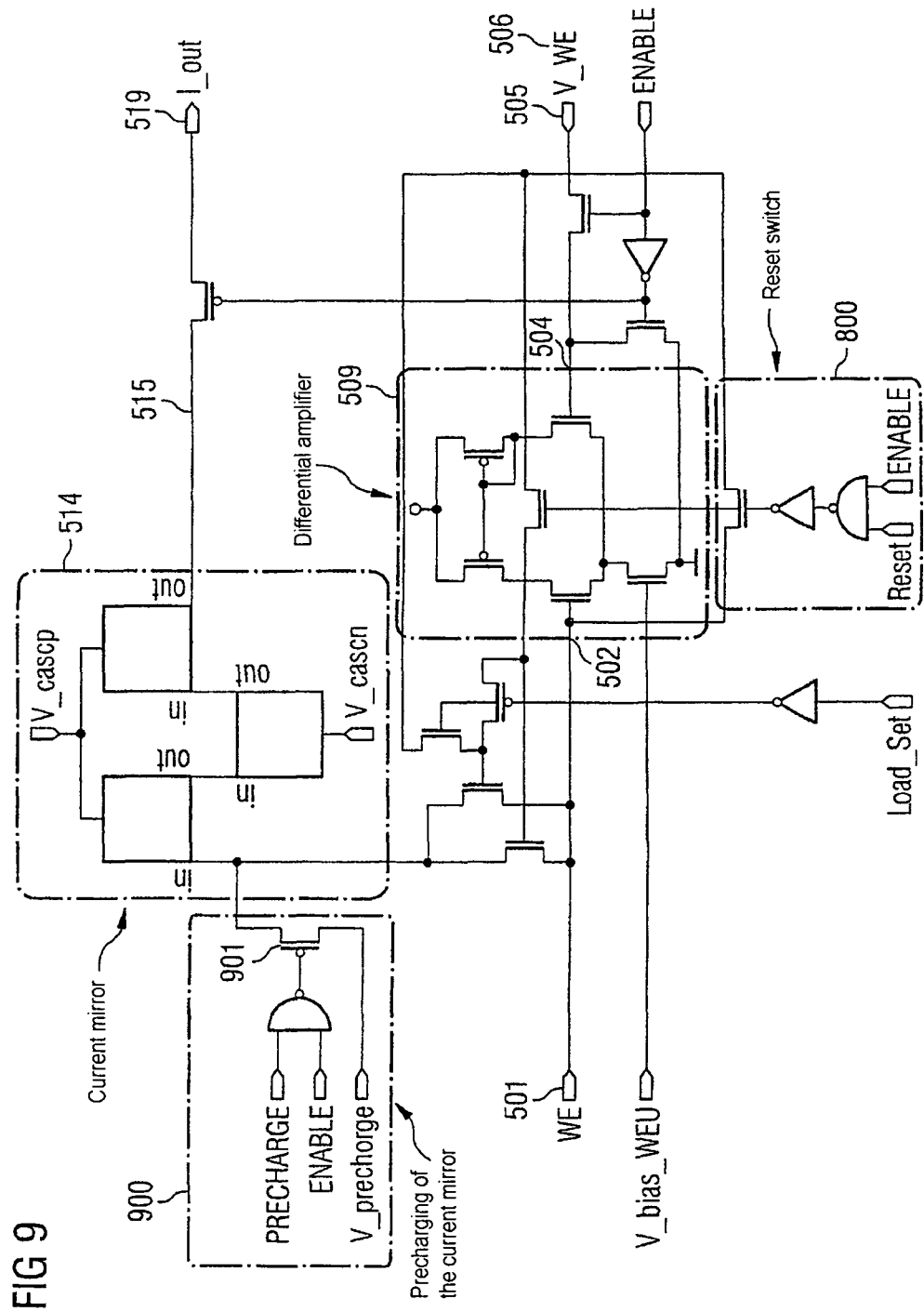
FIG. 9 shows a circuitry implementation of an operating circuit with a precharging circuit for precharging of the current mirror.

In one optional embodiment, as is illustrated in FIG. 9, additional switching elements can be provided, and these are advantageous for setting the edge gradient.

Figure 10:
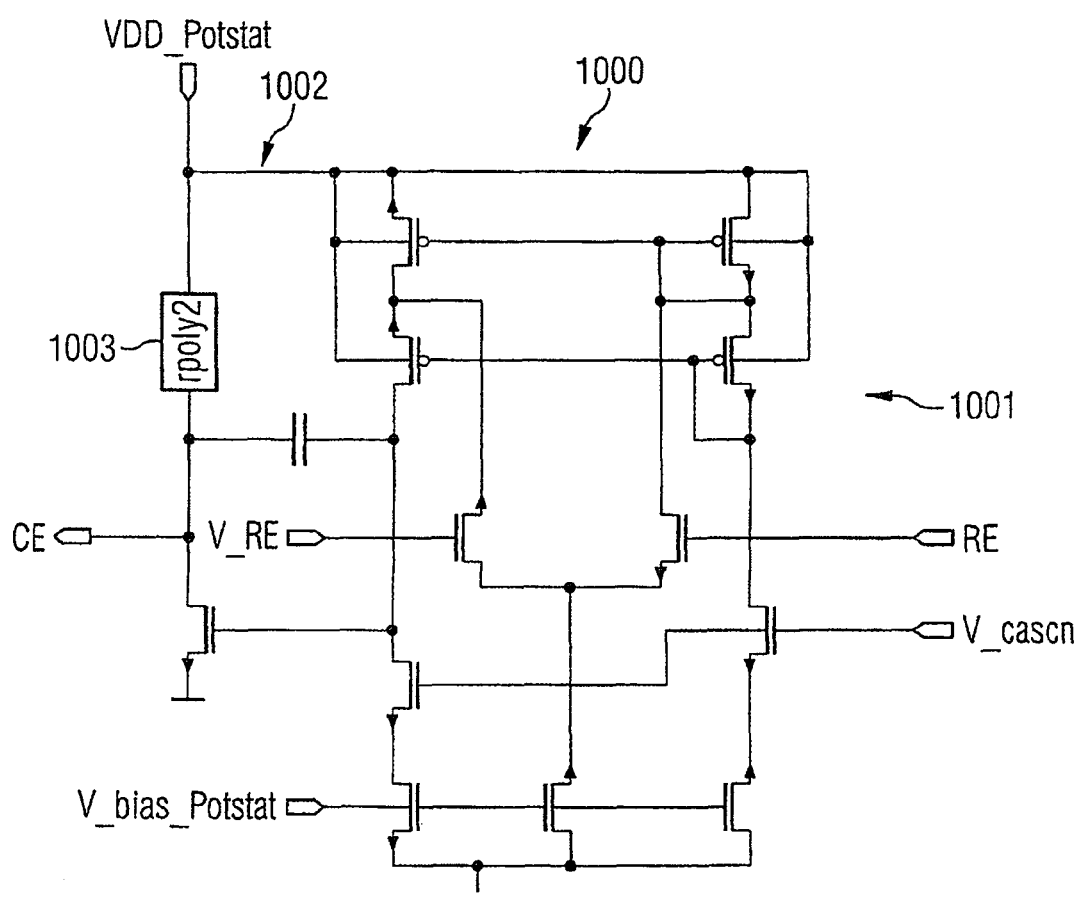
FIG. 10 shows a circuitry implementation of the potentiostat circuit according to one aspect of an embodiment of the invention.

The potentiostat circuit 1000 illustrated in FIG. 10 is used for monitoring the electrolyte potential.

For this purpose, a reference electrode is fitted in the reaction volume and measures the electrolyte potential, compares it with a reference voltage, and suitably sets the electrolyte potential via a large-area opposing electrode.

Since the potentiostat circuit 1000 in measurement methods according to an embodiment of the invention has to suddenly change the potential of the electrolyte, this, according to the invention, has a wide signal bandwidth and a high current driving capability.

Since the electrochemical system including the reference electrode/electrolyte/opposing electrode has complex electrical characteristics which are also dependent on the substances contained in the electrolyte, it is necessary to design the potentiostat circuit 1000 to be electrically highly stable, in order to avoid oscillations.

According to this refinement of the aspect of an embodiment of the invention, this was achieved by using a two-stage operational amplifier 1001, which has a non-reactive resistor 1003 in the positive output branch 1002. This admittedly on the one hand reduces the gain of the operational amplifier 1001, but allows stable operation up to high frequencies, with high output currents for capacitive loads at the same time.

In order to achieve a steep edge for the step-function voltage change, the analog step-function voltage change is not produced from outside the electronic chip, but the two electrical potentials are applied as a stable DC voltage signal to the electronic chip. After a trigger pulse, the input voltage to the potentiostat circuit 1000 is switched between the two DC voltage signal levels. The switching can take place very quickly and requires only one TTL signal (Transistor-Transistor-Logic-Signal).

If the sensors according to an embodiment of the invention are arranged in an array, then the individual sensors are addressed by way of row lines and column lines, as is shown by way of example in FIG. 1 for a sensor arrangement. The individual sensors can thus be driven and/or read selectively.

All sensor pixel circuits, such as those which are known per se in conjunction with redox cycling sensors, can be used in conjunction with the measurement principles described above.

In the situation in which no integrator is provided in one respective sensor pixel, the electric current which is measured and conditioned in the active pixel is passed via row lines or column lines to the edge of the sensor array where, after further signal processing, it can be passed in analog signal form or in digital signal form out of the electronic chip, or can be integrated in analog or digital form.

The sensor array is read successively in this way. Since one individual measurement requires only a time in the order of magnitude of 1 ms, the entire sensor array can be read comparatively quickly. In particular, a plurality of sensor pixels can be activated at the same time, if the appropriate number of comparators are provided.

An entire column or row is preferably activated, and the sensor signal is detected at the edge of the matrix. The electrode of all the inactive sensor pixels is switched so that no current flows, or its voltage with respect to the electrolyte potential is chosen in such a manner that no undesirable electrochemical reactions take place at this electrode.

If each of the sensor pixels contains one integrator, then, in principle, all of the sensor pixels can be activated at the same time, and the integration results can be checked successively in a subsequent time interval, by means of selection lines from the individual pixels.

Further electronic circuits for electrochemical operation of the sensor are located in the periphery of the sensor matrix, such as the potentiostat circuits as well as evaluation circuits for the analog measurement signals and/or digital measurement signals, for example analog/digital converters as well as digital circuits and analog circuits for driving the sensor array, as well.

Completely digital communication between the electrochemical analysis system according to an embodiment of the invention, that is to say the sensor arrangement and a peripheral reader, is particularly advantageous.

In this case in particular, an analog/digital converter is additionally provided for conversion of the analog measurement signal to a digital data signal, as well as a digital/analog converter for production of the required electrode voltage in the sensor arrangement, and these are monolithically integrated therein. Furthermore, in this case, a computation unit is provided for digital communication with the reader, as well as a communication interface to the sensor arrangement, for bidirectional data communication with the reader.

Figure 11:
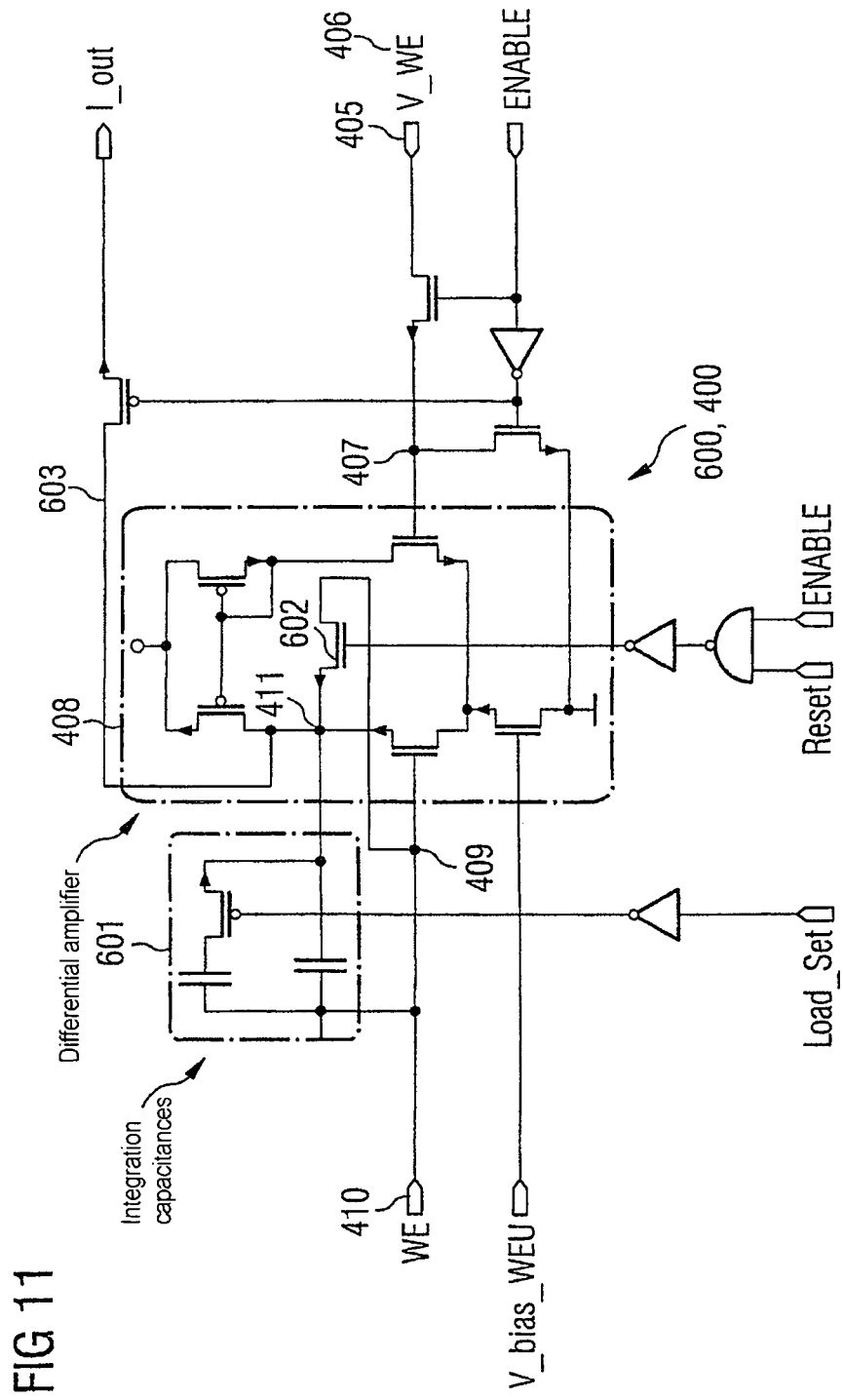
FIG. 11 shows a circuitry implementation of the pixel circuit as shown in FIG. 6.

FIG. 11 shows one circuitry implementation of the pixel circuit 600 as shown in FIG. 6.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The following publications are cited in this document:
[1] Hofmann, F. et al., "Passive DNA Sensor with Gold Electrodes Fabricated in a CMOS Backend Process", Proc. ESSDERC 2002, Digest of Techn. Papers, pages 487-490.
[2] Thewes, R. et al., "Sensor Arrays for Fully Electronic DNA Detection on CMOS", ISSC 2002, Digest of Techn. Papers, pages 350-351.
[3] Hintsche, R. et al., "Microelectrode Arrays and Application to Biosensing Devices", Biosensors and Bioelectronics, 1994, vol. 9, pages 697-705.
[4] Hintsche, R. et al., "Microbiosensors Using Electrodes Made in Si-Technology", Frontiers in Biosensorics, Fundamental Aspects, 1997, F. W. Scheller et al. (eds.), Dirk Hauser Verlag, Basel, pages 267-283.
[5] Paeschke, M. et al., "Voltametric Multichannel Measurements Using Silicon Fabricated Microelectrode Arrays", Electroanalysis, 1996, vol. 7, No. 1, pages 1-8.
[6] Found on the Internet on Mar. 31, 2004, at the following URL address:
http://www.combimatrix.com
[7] Found on the Internet on Mar. 31, 2004, at the following URL address:
http://www.frizbiochem.com
[8] DE 100 58 397 A1.
[9] U.S. Pat. No. 5,389,215.
[10] WO 02/097413 A2.
[11] US 2004/0045839 A1.
[12] WO 03/046209 A2.
[13] US 2004/0072223 A1.
[14] US 2003/0226768 A1.

LIST OF SYMBOLS

100 Pixel arrangement
101 Selection of the sensors in one column as active sensors
102 Electrodes of the other sensor arrangements
200 Pixel circuit
203 Column selection input
204 Row selection input
205 Third input for supply of a reference potential
206 Reference potential $V_{WE}$
207 First input of an operational amplifier
208 Operational amplifier
209 Second input of an operational amplifier
210 Working electrode
300 Alternative pixel circuit
400 Alternative pixel circuit
401 Oxidation integrator
402 Reduction integrator
403 First input
404 Second input
405 Third input
406 Reference potential $V_{WE}$
407 First input of an operational amplifier
408 Operational amplifier
409 Second input of an operational amplifier
410 Working electrode
411 Output of an operational amplifier
412 Control input
413 First controllable electrical resistor
414 Second controllable electrical resistor
415 Control connection
416 First output
417 Second output 418 Electrode current flowing through the working electrode
500 Alternative pixel circuit
501 Working electrode
502 First input of an operational amplifier
503 Operational amplifier
504 Second input of an operational amplifier
505 Third input of the pixel circuit
506 Reference potential $V_{WE}$
507 Column selection input
508 Row selection input
509 Output of an operational amplifier
510 Control connection
511 First controllable resistor
512 Control connection
513 Second controllable resistor
514 First current-mirror circuit
515 First output of the pixel circuit
516 Second current-mirror circuit
517 Second output of the pixel circuit
518 First switch
519 First current output signal $I_{ox}$
520 Oxidation integrator
521 Oxidation voltage $U_{ox}$
522 Second switch
523 Reduction output current $I_{red}$
524 Reduction integrator
525 Reduction output voltage $U_{red}$
600 Alternative pixel circuit
601 Feedback capacitor
602 Reset switch
603 Output of the pixel circuit
700 Alternative pixel circuit
701 Reference circuit
702 Input
703 Reference working electrode
704 First input of a reference operational amplifier
705 Reference operational amplifier
706 Second input of a reference operational amplifier
707 Output of a reference operational amplifier
708 Reference capacitor
709 Reference reset switch
710 Output of the reference circuit
711 Integrated reference signal $U_{ref}$
750 Coupling capacitor
800 Simple switch
900 Precharging unit
901 Switching transistor
1000 Potentiostat circuit
1001 Two-stage operational amplifier
1002 Positive output branch
1003 Non-reactive resistor

The invention claimed is:

1. A sensor array, comprising:
at least three electrodes forming a pixel arrangement, designed as biosensor arrangements for detection of biomolecules;
a potentiostat circuit; and
a switching unit, designed such that at least one of the at least three electrodes is selectively connected as a working electrode, which is coupled to an electrolytic analyte, the other electrodes of the at least three electrodes being connected as an opposing electrode, wherein each of the at least three electrodes can be alternatively connected as the working electrode or as the opposing electrode by the switching unit and the opposing electrode is exclusively formed by the other electrodes of the at least three electrodes of the pixel arrangement, not selected as the working electrode, and connected as the opposing electrode, the at least three electrodes being designed such that sensor events take place at an electrode, connected as the working electrode, of the at least three electrodes in an electrolyte solution when in the presence of the electrolytic analyte, wherein the sensor array is monolithically integrated at least one of in and on a substrate and wherein the switching unit deactivates an operating circuit of the selected working electrode and connects the selected working electrode to the selected opposing electrode via the potentiostat circuit.

2. The sensor array as claimed in claim 1, wherein the switching unit has at least one MOS transistor, which is provided within the sensor array.

3. The sensor array as claimed in claim 1, wherein each of the at least three electrodes is connected to an operating circuit provided outside the sensor array, and the operating circuit for the at least two electrodes which are connected as a common opposing electrode in the sensor array is driven such that an electrode potential follows a potential at the opposing electrode of the potentiostat circuit.

4. The sensor array as claimed in claim 1, further comprising a control circuit to at least one of drive, select and read at least one of the at least three electrodes.

5. The sensor array as claimed in claim 1, wherein the sensor array includes 50 to 1,000,000 electrodes.

6. The sensor array as claimed in claim 1, wherein a plurality of the at least three electrodes are designed for detection of substances which are at least one of oxidizable and reducible.

7. The sensor array as claimed in claim 1, wherein the sensor array is designed for detection of at least one of nucleic acid molecules, peptides and proteins.

8. The sensor array as claimed in claim 1, wherein capture molecules are immobilized on a surface of the electrodes.

9. The sensor array as claimed in claim 1, wherein the sensor array is designed such that a sensor signal is generatable via electrochemically active markings in the presence of an electrolytic analyte.

10. The sensor array as claimed in claim 9, wherein the electrochemically active markings have metal complex markings.

11. The sensor array as claimed in claim 10, wherein the electrochemically active markings have ferrocene markings.

12. The sensor array as claimed in claim 9, wherein the electrochemically active markings have ferrocene markings.

13. The sensor array as claimed in claim 1, wherein the opposing electrode is a counter electrode coupled to an electrolytic analyte and provides electrical charge carriers to set a known electrochemical potential of the analyte.

14. A method for operation of a sensor array which is monolithically integrated at least one of in and on a substrate in an electrochemical analysis method, wherein the sensor array includes at least three electrodes forming a pixel arrangement, a majority of the at least three electrodes being designed as a biosensor arrangements for detection of biomolecules, a potentiostat circuit, and includes a switching unit designed such that at least one of the at least three electrodes is selectively connected as a working electrode and the other electrodes of the at least three electrodes are connected as an opposing electrode, and wherein each of the at least three electrodes can be alternatively connected as the working electrode or as the opposing electrodes can be alternatively connected as the working electrode or as the opposing electrode by the switching unit and the opposing electrode is exclusively formed by the other electrodes of the at least three electrodes of the pixel arrangement connected as the opposing electrode, and the at least three electrodes are designed such that sensor events take place at one electrode, connected as the working electrode, of the at least three electrodes in an electrolyte solution when in presence of an electrolytic analyte, the method comprising:

(a) connecting at least two electrodes, of the at least three electrodes, to the opposing electrode connection of the potentiostat circuit, thus providing the opposing electrode of the sensor array monolithically integrated at least one of in and on the substrate;

(b) connecting at least one electrode of the at least three electrodes, as a working electrode for detection of the electrolytic analyte;

(c) connecting, after detection of the electrolytic analyte at the working electrode in (b), at least one of the at least three electrodes as a working electrode for detection of an electrolytic analyte;

(d) connecting at least one of the at least three electrodes according to (a) as an opposing electrode; and (e) repeating steps (a) to (d) as often as required;

wherein, before step (e) the switching unit deactivates an operating circuit of the selected working electrode and connects the selected working electrode to the selected opposing electrode via the potentiostat circuit.

15. The method for operation of a sensor array in an electrochemical analysis method as claimed in claim 14, wherein a total surface area of the electrodes which are connected as opposing electrode is at least ten times as large as a total surface area of the electrodes which are connected as working electrodes.

16. The method for operation of a sensor array in an electrochemical analysis method as claimed in claim 15, wherein at least one substance in an electrolyte is determined at least one of qualitatively and quantitatively on the basis of at least one of its characteristic oxidation and its characteristic reduction voltage via at least one of voltammetry, amperometry and coulometry.

17. The method for operation of a sensor array in electrochemical analysis method as claimed in claim 14, wherein at least one substance in an electrolyte is determined at least one of qualitatively and quantitatively on a basis of at least one of its characteristic oxidation and its characteristic reduction voltage via at least one of voltammetry, amperometry and coulometry.

18. The method for operation of a sensor array in an electrochemical analysis method as claimed in claim 14, wherein ferrocene-marked capture molecules are immobilized on the electrodes in order to analyze biomolecules, and a concentration of the biomolecules is determined by measurement of an amount of charge flowing during oxidation of the ferrocene.

19. The method for operation of a sensor array in an electrochemical analysis method as claimed in claim 14, wherein an external opposing electrode is additionally used in order to improve the time response of the overall system.

20. The method for operation of a sensor array in an electrochemical analysis method as claimed in claim 14, wherein the operating circuit of a working electrode is deactivated by use of a switching unit, for connection as an opposing electrode.

* * * * *